(12) United States Patent
Zhang et al.

(10) Patent No.: US 12,109,509 B2
(45) Date of Patent: Oct. 8, 2024

(54) **ULTRASONIC COMPOSITE ACIDIC WATER EXTRACTION METHOD FOR CORDYCEPS POLYSACCHARIDE AND CORDYCEPIN IN *CORDYCEPS MILITARIS***

(71) Applicant: JIANGNAN UNIVERSITY, Jiangsu (CN)

(72) Inventors: Min Zhang, Jiangsu (CN); Hao Shi, Jiangsu (CN); Sifu Yi, Jiangsu (CN); Xiaoling Guo, Jiangsu (CN); Lihua Hou, Jiangsu (CN); Wuxiong Yang, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 563 days.

(21) Appl. No.: 17/419,718

(22) PCT Filed: Dec. 6, 2019

(86) PCT No.: PCT/CN2019/123517
§ 371 (c)(1),
(2) Date: Jun. 30, 2021

(87) PCT Pub. No.: WO2020/177420
PCT Pub. Date: Sep. 10, 2020

(65) Prior Publication Data
US 2022/0080333 A1    Mar. 17, 2022

(30) Foreign Application Priority Data
Mar. 1, 2019    (CN) .......................... 201910156401.9

(51) Int. Cl.
| A23L 31/00 | (2016.01) |
| A01G 18/70 | (2018.01) |
| B01D 11/02 | (2006.01) |
| C08B 37/00 | (2006.01) |

(52) U.S. Cl.
CPC .......... *B01D 11/0265* (2013.01); *A01G 18/70* (2018.02); *A23L 31/00* (2016.08); *C08B 37/00* (2013.01)

(58) Field of Classification Search
CPC ...... A01G 18/70; B01D 11/0265; A23L 31/00
See application file for complete search history.

(56) References Cited

FOREIGN PATENT DOCUMENTS

| CN | 102499353 | 6/2012 |
| CN | 102558264 | 7/2012 |
| CN | 102850419 | 1/2013 |
| CN | 103601812 | 2/2014 |
| CN | 103751224 | 4/2014 |
| CN | 103755825 | 4/2014 |
| CN | 103800385 | 5/2014 |
| CN | 103936806 | 7/2014 |
| CN | 104694616 | 6/2015 |
| CN | 105085704 | 11/2015 |
| CN | 105273024 | 1/2016 |
| CN | 105504085 | 4/2016 |
| CN | 105614841 | 6/2016 |
| CN | 105669805 | 6/2016 |
| CN | 106317148 | 1/2017 |
| CN | 106749742 | 5/2017 |
| CN | 106810618 | 6/2017 |
| CN | 106866604 | 6/2017 |
| CN | 107183710 | 9/2017 |
| CN | 107602721 | 1/2018 |
| CN | 107674104 | 2/2018 |
| CN | 108926580 | 12/2018 |
| CN | 109810201 | 5/2019 |

OTHER PUBLICATIONS

Machine translation of CN104694616. pp. 1-11. (Year: 2015).*
Machine translation of CN105273024. pp. 1-8. (Year: 2016).*
Machine translation of CN105504085. pp. 1-9. (Year: 2016).*
Machine translation of CN107674104. pp. 1-2. (Year: 2017).*
Kang et al. "Optimization of large scale culture conditions for the production of cordycepin with Cordyceps militaris by liquid static culture". The Scientific World Journal. vol. 2014. pp. 1-16. (Year: 2014).*
Wang, et al. "Effect of Cordyceps militaris waster medium on production performance, egg traits and egg yolk cholesterol of laying hens". Japan Poultry Sci., 52: 188-196, 2015. (Year: 2015).*
Yang, Fan, "Production and isolation of cordycepin from solid state fermentation," Master's Thesis, Jun. 2017, School of Biotechnology, Jiangnan University.

(Continued)

*Primary Examiner* — Jenna A Watts
(74) *Attorney, Agent, or Firm* — JCIP GLOBAL INC.

(57) ABSTRACT

Disclosed is an ultrasonic composite acidic water extraction method for a *Cordyceps* polysaccharide and cordycepin in *Cordyceps militaris*, which falls within the technical field of food processing. The method comprises: picking, washing, drying, pulverizing and degreasing *Cordyceps militaris* fruiting bodies to obtain a *Cordyceps militaris* dry powder; then immersing same in a prepared diluted hydrochloric acid solution to perform three cycles of ultra-low temperature freezing and microwave defrosting, and at the same time using low-frequency ultrasonic waves to carry out assisted stirring and extraction; then subjecting an extract to evaporation and concentration treatments; and finally, performing freeze-drying on the extract to collect a dry powder of a water extraction product. The amount of an additive used in the method meets domestic and foreign usage requirements of food additives, and the operation is simple, practical and uses a combination of chemical and physical methods, thereby saving time and being highly efficient.

16 Claims, No Drawings

(56) References Cited

OTHER PUBLICATIONS

Wu, Ying-Ming et al., "Effect on the Distill of Polysaccharides in Ganoderma Lucidum Spore Powder Treated with Ultrasonic and Thawing and Freezing Test of Ultra-low Temperature," Edible Fungi of China, vol. 27, Dec. 2008, pp.34-35.
"International Search Report (Form PCT/ISA/210) of PCT/CN2019/123517", mailed on Feb. 27, 2020, with English translation thereof, pp. 1-6.
"Written Opinion of the International Searching Authourity (Form/ISA/237) of PCT/CN2019/123517", mailed on Feb. 27, 2020, pp. 1-5.

* cited by examiner

ULTRASONIC COMPOSITE ACIDIC WATER EXTRACTION METHOD FOR CORDYCEPS POLYSACCHARIDE AND CORDYCEPIN IN CORDYCEPS MILITARIS

CROSS-REFERENCE TO RELATED APPLICATION

This application is a 371 of international application of PCT application serial no. PCT/CN2019/123517, filed on Dec. 6, 2019, which claims the priority benefit of China application no. 201910156401.9, filed on Mar. 1, 2019. The entirety of each of the above-mentioned patent applications is hereby incorporated by reference herein and made a part of this specification.

BACKGROUND OF THE INVENTION

1. Technical Field

The present invention relates to an ultrasonic composite acidic water extraction method for a *Cordyceps* polysaccharide and cordycepin in *Cordyceps militaris*, which falls within the technical field of food processing.

2. Description of Related Art

*Cordyceps militaris* (CM), commonly known as northern *Cordyceps sinensis*, is a traditional edible and medicinal mushroom in China, is a fungus belonging to the Ascomycota phylum and the Pyrethroid family, and is shown to have a similar pharmacological effect to *Cordyceps sinensis*. *Cordyceps militaris* has been used for hundreds of years in many Asian countries, especially in China. It contains abundant special natural ingredients with biological and pharmacological activities, such as cordycepin (3'-deoxyadenosine), adenosine, cordycepic acid, SOD enzyme and a *Cordyceps* polysaccharide. In traditional Chinese medicine, it is believed that water extracts of Chinese herbs have the functions of nourishing lung and kidney, relieving pain in waist and knees, helping patients to recover from an illness, etc. Studies in recent years also confirm these viewpoints. Among these natural active compounds, cordycepin is an important immunomodulatory active compound which affects the effects of immune cells and cytokine networks and has a function of resisting the ischemia-reperfusion injury. Cordycepin can inhibit the growth of mouse melanoma cells and improve the injury of testis without causing side effects. A *Cordyceps* polysaccharide effectively improves the immune function by protecting the body from an oxidative stress, and its hypoglycemic effect is even stronger than that of *Cordyceps sinensis* polysaccharide.

In most extraction processes for the active ingredients of herbaceous plants, the extraction techniques often used mainly include methods such as hot water reflux extraction, ultrasonic-assisted extraction, microwave-assisted extraction, enzymolysis extraction, ultrahigh-pressure extraction and supercritical liquid extraction. Therein, the major factors affecting water extracts (predominantly cordycepin and a *Cordyceps* polysaccharide) of *Cordyceps* include the type of extractant, extraction time, extraction temperature, material-liquid ratio, extraction times, auxiliary technical parameters, etc. Because most studies have adopted one or two extraction methods to obtain active ingredients cordycepin or *Cordyceps* polysaccharide that are relatively single, and the extraction yield is relatively low. Meanwhile, impurities such as chloroform, n-butyl alcohol, ethyl acetate and non-food-grade chemical reagents may be introduced in the processes of separation and purification, which will bring troubles to impurity removal of the active ingredients of *Cordyceps militaris* and also bring greater hidden dangers to food safety.

From literature reports, solvents such as ethanol, deionized water, petroleum ether, trichloromethane, PEG and n-butyl alcohol are mainly selected as extractant for *Cordyceps militaris* fruiting bodies, and these extractants have respective advantages and disadvantages. When petroleum ether is used as an extractant, a large quantity of fat-soluble substances in *Cordyceps* are precipitated, and polar substances such as cordycepin and *Cordyceps* polysaccharide are hard to separate; the organic solvents such as trichloromethane have toxicity and thus affect the physical health of an operator and also impose higher requirements on the protective measures, thereby increasing the cost of supporting facilities. As a result, deionized water or an ethanol aqueous solution is generally adopted as an extractant, where a single ingredient is obtained, subsequent separation and purification are required due to the relatively complicated ingredients in the dissolved substances, resulting in a complicated process and a relatively high cost; however, for obtaining water-soluble substances in *Cordyceps militaris*, using water or alcohol as a solvent can just increase the precipitation of the active ingredients in the fruiting bodies. Studies have found that, compared with an acid thermal extraction method, a microwave extraction method, an acid thermal microwave extraction method and an acetone extraction method, an acid thermal ultrasonic extraction method has the highest yield in extracting the substances such as carotene in *Cordyceps militaris*. In accordance with the similar compatible principle and the isoelectric point principle, when an acidic solution is used to extract *Cordyceps militaris* fruiting bodies, the final yield of water-soluble active substances can be increased by increasing the solubility of polar water-soluble substances in the extraction solvent.

The freezing-defrosting extraction technique is an extraction method which increases the dissolution of active ingredients by damaging cellular structures in a physical freezing-defrosting process. Under a low-temperature condition, an intracellular solution, especially an aqueous solution of a material forms an intracellular ice crystal which increases the cell volume, breaks a hydrophobic bond structure of the cell membrane and then breaks the cell membrane and cell wall; and when in defrosting, a large temperature difference is generated between the inner and outer sides of the cell wall, which generates a thermal shock stress to break the cell wall again. Multiple cycles of the freezing-defrosting process seriously damage the structures such as the cell walls of the material, and finally increase the release, spreading and dissolution of intracellular substances, thereby promoting the dissolution of active water-soluble ingredients.

The ultrasonic extraction technique breaks the tissue structures mainly through the mechanical crushing and the cavitation effect of ultrasonic waves, and promotes the extracts to spread from a raw material to a solvent. When ultrasonic waves propagates in a liquid medium, the liquid medium is subjected to constant stretching and compression to form cavitation bubbles, and the cavitation bubbles continue to increase until they rupture, and multiple effects such as cavitation effect, high shear force, crushing and agitation are generated instantaneously. Therein, in addition to damaging the cell wall, the cavitation effect also causes the microflow inside a cell to generate a shearing force. In addition, the cavitation effect can also induce generation of H• free radicals and •OH free radicals in a water medium to attack the chemical structure of the cell wall, thereby reducing its mechanical strength, making it more fragile and allowing the content to flow out more easily. Meanwhile, in combination with the freezing-defrosting cyclic extraction technique, the dissolution and acquisition of active ingredients in a material are effectively improved.

Deng, Hua (China Patent Application No.: 201410199236.2) discloses a process method for extracting cordycepin from *Cordyceps militaris* by alcohol extraction, concentrating, dewaxing, purifying, liquid membrane extraction, refining and drying. Compared with the prior art, the process is simplest and short in production period; an organic solvent is small in usage amount and is reusable; high product yield is achieved. Compared with the present invention, this extraction method is more complicated, and has high cost in preparing a liquid membrane, certain requirements on extraction operators, and high equipment maintenance cost during production.

Zhang, Yaozhou et al. (China Patent Application No.: 201410041853.X) provide a method for extracting a cordycepin component from *Cordyceps militaris*, which includes the following steps: ultrafinely pulverizing *Cordyceps militaris* fruiting bodies to obtain superfine powder; performing water extraction on the superfine powder using ultrapure water and drying the supernatant, and then performing alcohol precipitation with ethanol, centrifuging, and collecting the alcohol precipitation supernatant, and performing rotary evaporation on the alcohol preparation supernatant, and drying to obtain a crude extract; dissolving the crude extract in a 15% methanol-water solution to 100 mg/mL, separating through a preparative liquid phase DAC reversed phase column under the following conditions: reversed phase separation packing, C18; elution, gradient elution with 5-15% methanol-water solution and then isocratic elution with 15% methanol-water solution, detection wavelength, 260 nm, and screening the obtained components for in-vitro antitumor activity, and selecting the component with the strongest activity, i.e. target cordycepin component. The method is simple, controllable and highly reproducible, the content of cordycepin in the obtained component is high, and the batch quality is stable; however, methanol reagent may be introduced in the separation and purification processes, and further crystallization treatment is not performed after the elution and separation by preparative chromatography, and thus the resulting solution is not easy to store. In contrast, in the present method, the water extract crystallizes into powder after freeze-drying, which is convenient for packaging the finished product.

Zhang, Yaozhou et al. (China Patent Application No.: 201410041854.4) provide a method for extracting antitumor active components from *Cordyceps militaris*, which includes: performing ultra-low temperature pulverizing on *Cordyceps militaris* fruiting bodies; extracting the obtained superfine powder by poaching, precipitating and extracting with acetone; dissolving the obtained precipitate, and then performing liquid chromatography, where the elution reagents are 100% n-hexane, 25% ethyl acetate-n-hexane, and 100% ethyl acetate; subjecting the component with the strongest activity to liquid chromatography, where the elution reagents are 100% n-hexane, 10% ethyl acetate-n-hexane, 15% ethyl acetate-n-hexane, 30% ethyl acetate-n-hexane and 60% ethyl acetate-n-hexane; subjecting the component with the strongest activity to liquid chromatography, where the elution reagents are 100% dichloromethane and 25% dichloromethane-methanol; and subjecting the component with the strongest activity to liquid chromatography, where the elution reagents are 100% n-hexane and 5% ethanol-n-hexane; and selecting the component with the strongest activity, i.e. target component of this invention. Although this method has good repeatability, organic reagents such as n-hexane and ethyl acetate are introduced in the extraction and elution processes, which increases the difficulty of the subsequent removal of impurities.

Kou, Keming and Peng, Yanmei (China Patent Application No.: 201310592568.2) invented a method for extracting cordycepin and a *Cordyceps* polysaccharide from *Cordyceps militaris* using a macroporous adsorption resin, which includes: pulverizing *Cordyceps militaris* fruiting bodies, and extracting with water; concentrating an extract; then adding ethanol, and standing still to precipitate a *Cordyceps* polysaccharide and obtain a supernatant; passing the supernatant through a macroporous adsorption resin column to obtain an eluent; and concentrating and drying the eluent to obtain a cordycepin extract. The product obtained by the method of this invention contains few organic solvent residues; however, the desorption capacity of the resin filler has been not studied in the elution process with the macroporous resin, and the problems of filler blockage and aging exist in the repeated use of the macroporous resin, thereby affecting the lifetime of the resin. In contrast, the present method imposes lower requirements on an extraction container, and is suitable for industrial production.

Li, Fuquan et al. (China Patent Application No.: 201210014073.7) invented a method for extracting cordycepin and a *Cordyceps* polysaccharide from *Cordyceps militaris*, which includes the steps of: water extraction, alcohol extraction, column extraction of a supernatant, and column extraction of a precipitate. In the water extraction step of this method, the water temperature is set at 55-58° C., which can make the active ingredients in *cordyceps* sufficiently dissolved while preventing the cordycepin from being decomposed; and thus, extracting cordycepin and a *Cordyceps* polysaccharide at such water temperature can avoid waste of resources. The method extracts cordycepin and a *Cordyceps* polysaccharide at the same time and is of reference significance for high utilization of active substances of *Cordyceps militaris*. However, compared with the present invention, the method has longer extraction time and complicated extraction process, which needs to be further optimized.

Hua, Chun et al. (China Patent Application No.: 201410002259.X) provide a method for extracting a *Cordyceps militaris* stroma polysaccharide from a waste *Cordyceps militaris* culture medium, and use of an extract. The invention achieves the extraction of the *Cordyceps militaris* stroma polysaccharide from the waste *Cordyceps militaris* culture medium through the experimental steps of performing enzymolysis, microwave treatment and centrifugal separation, adding ethanol for precipitation, and then removing starch and protein and performing gel column purification and the like. The obtained polysaccharide extract has high purity, and the waste *Cordyceps militaris* culture medium is effectively utilized; however, the active substances such as cordycepin are lost in the extraction process. Compared with the present method, the method of Hua, Chun et al. needs further improvement in the degree of waste utilization.

The invention of Qiu, Yingchao et al. (China Patent Application No.: 201610123035.3) discloses a enzymolysis-assisted method for extracting cordycepin from a waste *Cordyceps militaris* culture medium, which includes by using a waste *Cordyceps militaris* culture medium as a raw material, performing high-pressure treatment and then enzymolysis using a neutral protease; then adding hot water for enzyme deactivation, and leaching; removing impurities through resin adsorption, and then performing dialysis and concentration; and crystallizing in an ice bath and then performing freeze-drying to obtain cordycepin from the waste *Cordyceps militaris* culture medium. This invention achieves the reuse of a waste culture medium, thereby saving the production cost. However, compared with the present invention, the method has a relatively low degree of protease utilization, and thus may increase the cost of other raw materials.

Gao, Zhaojian et al. (China Patent Application No.: 201710009796.0) disclose a method for extracting and continuously enriching polysaccharides from culture media for *Cordyceps militaris*, which includes: drying of the rice residual culture media for *Cordyceps militaris*, superfine pulverizing, enzymatic hydrolysis by the aid of a biological multi-enzyme system, centrifugal filtration, control of backflow, concentration and enrichment using a multifunctional membrane, spray drying, and qualitative and quantitative analysis, thereby establishing a rapid, efficient and economical separation method for a *Cordyceps* polysaccharide. The invention makes an effective use of a waste *Cordyceps militaris* culture medium, thereby saving the resources and cost. The present invention is suitable for large-scale industrial production. The use of superfine pulverizing and membrane separation techniques has a great effect on the dissolution of active substances and the collection of cordycepin components, and has a reference value for the improvement of the present invention.

Su, Liuhua (China Patent Application No.: 201210353679.3) discloses a method for extracting cordycepin and a polysaccharide from *Cordyceps militaris*, which includes: pulverizing a raw material of *Cordyceps militaris*, and then filling into a subcritical extraction kettle; introducing deionized water; performing countercurrent extraction for 10-60 min at a temperature of 100-200° C. and under a pressure of 1-15 MPa, to obtain an extract; concentrating the extract, and then adding 95% ethanol in 5-6 times the volume of the concentrate; sufficiently stirring for sufficient precipitation; dissolving the precipitate with water again; adding trichloroacetic acid with the concentration of 3-10% to remove a protein; performing alcohol precipitation again, and drying to obtain a *Cordyceps* polysaccharide; combining the twice alcohol precipitates, and concentrating under reduced pressure to be free from alcohol; adding into an active carbon column for adsorption; eluting with an ethanol solution; concentrating an eluent under reduced pressure; standing for crystallization; and drying the crystal to obtain the cordycepin. This invention realizes high utilization of *Cordyceps militaris*, and improves the yields of *Cordyceps* polysaccharide and cordycepin; however, compared with the present invention, the subcritical extraction technique imposes higher requirements on extraction equipment and operators, and thus may increase the production cost to some degree.

Dong, Chao (China Patent Application No.: 201610605098.2) discloses a method for extracting cordycepin from *Cordyceps militaris*, which mainly includes the steps: degreasing with petroleum ether, extraction with high-concentration ethanol, extraction with ethyl acetate, and twice purification with D1400 resin, so that the cordycepin with a purity of greater than or equal to 95% can be obtained. This invention has the advantages of easy operations and a high extraction rate of cordycepin, but only the cordycepin in *Cordyceps militaris* is extracted and cordycepin polysaccharides and other substances are greatly lost.

Liu, Hongfei (China Patent Application No.: 201610082656.1) discloses a method for preparing a *Cordyceps militaris* extract rich in bioactive substances, which falls within the field of functional foods. The method includes: preparing a *Cordyceps militaris* bioconversion composite enzyme system containing the biological enzymes such as superoxide dismutase, glycosidase, transferase, hydrolase and isomerase; performing a hydrolysis reaction of the *Cordyceps militaris* composite enzyme system; performing efficient, dynamic and cyclic extraction of the bioactive substances of *Cordyceps militaris*; filtering with a microfiltration membrane; and performing vacuum concentration under reduced pressure, to obtain the *Cordyceps militaris* extract rich in bioactive substances. Compared with the currently disclosed methods for preparing a *Cordyceps militaris* extract, this method remarkably increases the contents of the bioactive substances such as cordycepin, cordycepic acid, *Cordyceps* polysaccharide and adenosine in the extract. However, compared with the present invention, the composite enzyme system prepared in this invention has a complicated process and harsh environmental requirements, thereby greatly increasing the manufacturing cost of extraction equipment and the cost of enzyme preparations.

Tang, Qingjiu et al. (China Patent Application No.: 201510585474.1) disclose a method for preparing an active polysaccharide of *Cordyceps militaris*, which includes: performing superfine pulverizing on *Cordyceps militaris* fruiting bodies, then extracting with boiling water, and collecting the supernatant; concentrating the supernatant, then adding ethanol for precipitation; passing the precipitated part through a DEAE-sepharose column; and desalting a part of 0-0.5 N, and then performing freeze-drying to obtain the active polysaccharide of *Cordyceps militaris*. The method is easy to operate and has a reference value.

Yin, Ming et al. (China Patent Application No.: 201710788899.1) disclose a method for extracting cordycepin in *Cordyceps militaris*, which includes: soaking *Cordyceps militaris* for 35-40 min in an aqueous citric acid solution; performing microwave drying; then, mixing same with an appropriate amount of purified water and cellulase for enzymolysis; filtering to obtain a filtrate; and finally, performing acidification, alcohol extraction and spray drying to obtain the cordycepin. This invention adopts soaking in citric acid and microwave drying and is similar to the present invention in terms of enhancing the extraction rate of cordycepin and enhancing the dissolution of active substances of *Cordyceps militaris*, but needs to be further optimized due to strict requirements on the environmental conditions such as temperature and pressure in the enzymolysis process.

Kang, Wenyi (China Patent Application No.: 201710033639.3) discloses a method for extracting a *Cordyceps militaris* polysaccharide, which includes: decocting *Cordyceps militaris* in water, filtering, adding absolute ethanol into the filtrate until the final concentration of ethanol is 70±5 V %, standing, and performing solid-liquid separation, where the obtained precipitate is the *Cordyceps militaris* polysaccharide. The invention consumes a huge volume of ethanol and only uses a boiling water bath for extraction, which takes a long time and has low efficiency; and the content of other components except *cordyceps* polysaccharide in the extracted product is relatively high, and the purity of the polysaccharide is low.

Sun, Junshe and Pei, Haisheng (China Patent Application No.: 201710322120.7) disclose a method for extracting and purifying walnut green husk polyphenols using acidic electrolyzed water, which mainly includes the following steps:

mixing, mashing and homogenizing fresh walnut green husks with acidic electrolyzed water to obtain a slurry; stirring and leaching the slurry to obtain a stirred extract; performing residue-liquid separation on the stirred extract; adding acidic electrolyzed water again into the separated solid residue, and performing second stirring and leaching; mixing the liquid phases separated after twice stirring and leaching, and passing the mixed liquid phases through a macroporous adsorption resin at a controlled flow rate; eluting polyphenols adsorbed onto the resin by means of an ethanol solution after the mixed liquid phases flow through the macroporous adsorption resin; and then distilling an eluent, and recycling ethanol, to obtain high-purity walnut polyphenols. The invention performs extraction and purification on the walnut polyphenols, and the obtained product has high purity. Compared with the invention, the acidic water extraction of *Cordyceps militaris* in the present research provides abundant active ingredients, and reduces purification and impurity removal processes for a single active ingredient, thus being suitable for large-scale extraction of crude water extracts of *Cordyceps* in a factory, and reducing the cost of subsequent downstream processing.

Ding, Zhansheng et al. (China Patent Application No.: 201110365289.3) disclose a method for efficiently separating and extracting and stably storing bayberry polyphenols. The invention uses acidic water with a pH of 3.5-4.0 as extractant, and extracts polyphenols from bayberry pomace and juice through multiple mashing and centrifugation of the bayberry raw materials. The method mainly includes: adsorption with a macroporous adsorption resin, evaporation and concentration to remove alcohol, adding of maltodextrin, and freeze-drying. The invention uses water as extractant, which reduces the cost of impurity removal in the subsequent purification process. Compared with the invention, the present work uses the acidic aqueous solution to extract active substances such as cordycepin and cordycepin polysaccharides with a high extraction rate in the water extract, simple operation process and low production cost.

Yang, Jie et al. (China Patent Application No.: 201711021626.0) provide a method for extracting a tremella polysaccharide using an acidic buffer solution, which includes the following steps: leaching tremella powder with an acidic buffer solution under a heating condition, to obtain a leach liquor; performing solid-liquid separation on the leach liquor, to obtain a liquid component which contains a tremella polysaccharide; and performing alcohol precipitation on the liquid component, where the obtained precipitate is the tremella polysaccharide. This invention extracts a high content of a polysaccharide, and also thus proves the feasibility of extracting polysaccharides from herbal plants or edible fungi using acidic aqueous solutions. The present invention just adopts an acidic water solution combined with ultrasonic waves to assist the extraction of water-soluble active ingredients such as cordycepin and *Cordyceps* polysaccharide in *Cordyceps militaris*, which is simple in process and suitable for industrial applications.

Zhu, Zhou et al. (China Patent Application No.: 201710126525.3) disclose a method for extracting potato anthocyanin, which includes the following steps: a) in the presence of ascorbic acid, mixing potatoes with a first acidic solution to obtain a potato slurry; b) sequentially performing a first filtration, addition of an enzyme preparation to reduce viscosity, a first centrifugation to remove a precipitate, and a second filtration on the potato slurry; c) adsorbing a crude anthocyanin extract through a macroporous desorption resin and eluting the crude anthocyanin extract with water and ethanol, respectively; and d) sequentially concentrating and drying the resulting desorbed liquid, to obtain the anthocyanin. The invention uses ascorbic acid as an acidic solvent to extract the anthocyanin component in potatoes, which improves the stability of the potato anthocyanin in a mixed extract; and in contrast, the present invention uses citric acid or edible hydrochloric acid as an acidic extractant, which is more economical in production cost, and is added within the scope of national standards without any side effects on the human body.

SUMMARY OF THE INVENTION

Technical Problem

An objective of the present invention is to provide an ultrasonic composite acidic water extraction method for a water extract of *Cordyceps militaris* fruiting bodies, so as to solve the problems of the prior art.

Technical Solution

The technical solution of the present invention:

An ultrasonic composite acidic water extraction method for a *Cordyceps* polysaccharide and cordycepin in *Cordyceps militaris* includes: picking, washing, drying, pulverizing and degreasing *Cordyceps militaris* fruiting bodies to obtain a *Cordyceps militaris* leftover dry powder; then immersing same in a prepared diluted acid solution to perform multiple freezing-defrosting cycles of ultra-low temperature freezing and microwave defrosting, and at the same time using low-frequency ultrasonic waves to carry out assisted stirring and extraction; then subjecting an extract to evaporation and concentration treatments; and finally, performing freeze-drying on the extract to collect a dry powder of a water extraction product, which includes the following specific steps:

(1) culturing and harvesting: culturing *Cordyceps militaris* fruiting bodies in a solid medium, harvesting after 40-45 days of the culturing, and storing the harvested fruiting bodies under refrigeration at 4° C.;

(2) washing and drying: drying the harvested *Cordyceps militaris* fruiting bodies for 5 hours in a hot-air drying oven at 60-65° C. during which the *Cordyceps militaris* fruiting bodies are arranged evenly and kept ventilated; and collecting and storing same in a cool and dry place after drying to a constant weight;

(3) pulverizing: crushing a dry sample of *Cordyceps militaris*, and passing through a 60-mesh sieve;

(4) degreasing: placing the pulverized sample in a reflux device, performing reflux extraction with 95% ethanol at a material-liquid ratio of 1:5 (w:v) in a boiling water bath for 3 hours, centrifugation, collecting the precipitate, and drying at 60-65° C. to a constant weight, to obtain a degreased *Cordyceps* powder;

(5) ultra-low temperature freezing-microwave defrosting cycle: adding distilled water into the degreased *Cordyceps* powder at a material-liquid ratio of 1:40 (w:v), to obtain an extract; stirring and titrating with a 1 mol/L diluted acid solution to make the pH of the extract reaches 4.8±0.2; freezing the extract for 2 hours at −80° C.; taking out the extract, and defrosting for 2 min in microwaves with a power of 300-400 W; and repeating the freezing-defrosting operation three times, to obtain a crude extraction mixture of *Cordyceps militaris*;

(6) ultrasonic-assisted extraction: after obtaining the crude extraction mixture of *Cordyceps militaris*, extracting for 35-40 min at 65-70° C. with the assistance of ultrasonic waves having a frequency of 20-30 KHz and a power of 300-400 W; and after the extraction is complete, centrifuging for 15 min at 4,000 r/min, and filtering the supernatant to obtain a crude water extract of the *Cordyceps militaris* fruiting bodies;

(7) evaporation and concentration: concentrating, by rotary evaporation at 60-65° C. and at 0.095 MPa, the crude water extract of the *Cordyceps militaris* fruiting bodies to 1% of the original volume, until it finally becomes a viscous and thick slurry; collecting the concentrate, and freezing for 24 hours at −70° C.; and (8) freeze-drying to prepare powder: performing freeze-drying on the frozen concentrate of *Cordyceps militaris* for 3 h in a cold trap at −55° C., to obtain a dry powder of the water extract of *Cordyceps militaris*.

In the step (1), the components of the solid medium include rice, wheat, glucose, potassium dihydrogen phosphate, magnesium sulfate heptahydrate, vitamin B1 and vitamin B2.

In the step (1), the height of the harvested *Cordyceps militaris* fruiting bodies is greater than or equal to 7 cm.

In the step (3), the dry sample of *Cordyceps militaris* is cut into segments of 3-4 cm for crushing, and then is pulverized.

In the step (4), the speed of centrifugation is 4,000 r/min, and the time of centrifugation is 20 min.

In the step (5), the diluted acid solution is a diluted hydrochloric acid solution, a citric acid solution or an acetic acid solution.

Principle: the present method adopts a food-grade diluted hydrochloric acid solution to regulate the pH value of an extract, and acquires, based on studies, the solution conditions away from the optimum dissolution isoelectric points of cordycepin and *Cordyceps* polysaccharide in *Cordyceps militaris*, so as to increase the solubility of water-soluble active ingredients in *Cordyceps militaris* under the same temperature conditions. Proper times of freezing and defrosting can break a hydrophobic bond structure of the cell membrane to damage the cell membrane and the cell wall; and in addition, the increase of intracellular water crystals causes the cells to swell and rapture, and intracellular substances are dissolved out after defrosting, thereby increasing the dissolution rate of the intracellular water-soluble ingredients of *Cordyceps militaris*. With the assistance of the low-frequency ultrasonic technique, the wall breaking effect of powder can be enhanced in the extraction process, and the aggregation effect of the powder in a solvent can be effectively reduced, thereby increasing the final yield of an active water extract in the *Cordyceps militaris* fruiting bodies, and effectively saving the extraction time. Freeze-drying is finally performed to obtain the dry powder of a water extract of *Cordyceps militaris*, which can effectively prevent the decomposition and denaturation of some heat-sensitive active ingredients, so as to preserve the bioactivity of the extraction product. The present invention improves a general method for extracting Chinese herbs or medicinal fungi, so that compared with a hot water reflux extraction method, the extraction time is reduced by about 33%, and the yields of *Cordyceps* polysaccharide and cordycepin are increased from 8.72 g/100 g and 4.422 mg/g to 10.13 g/100 g and 5.794 mg/g respectively; and at the same time, the problem of powder aggregation is reduced in a water extraction process of *Cordyceps militaris*, and the active ingredients in *Cordyceps militaris* are effectively preserved.

ADVANTAGEOUS EFFECT OF THE INVENTION

Advantageous Effect

Advantageous effects of the present invention: the present invention mainly adopts a combination of ultrasonic waves and acidic water to extract water-soluble substances such as cordycepin and *Cordyceps* polysaccharide in *Cordyceps militaris*. Compared with traditional extraction with an organic solvent, the introduction of organic impurities in a water extraction product can be reduced, and the manpower and material costs are reduced in the subsequent impurity removal process; the use of the ultra-low temperature freezing-microwave defrosting technique enhances the destructive effect on the cellular structures of *Cordyceps*, and increases the dissolution of active ingredients; and the multiple mechanical and physical actions of freezing-defrosting wall breaking combined with ultrasonic-assisted extraction technique effectively avoid the introduction and residue of organic chemical reagents. The present invention is of a reference significance to overcome the shortcomings of a low extraction rate and many impurities in an extract in the current water extraction processes of *Cordyceps militaris*.

DETAILED DESCRIPTION OF THE EMBODIMENTS

Detailed Description of the Present Invention

The technical solution of the present invention is further described below in connection with specific examples.

Example 1: Using a diluted hydrochloric acid solution as extractant, in combination with ultra-low temperature freezing-defrosting and low-frequency ultrasonic technique to assist in the extraction of a *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder, then the dry powder was immersed in a prepared diluted hydrochloric acid solution (pH=4.8), and subjected to three cycles of ultra-low temperature freezing (−80° C.) and microwave defrosting (400 W, for 2 min), and at the same time, with assistance of low-frequency ultrasonic waves (having a frequency of 20-30 KHz, and a power of 350 W), stirred and extracted for 40 min at 65° C.; then an extract was concentrated to 1% of original volume by rotary evaporation at 60° C. and at 0.095 MPa; the concentrate was collected and frozen for 24 hours at −70° C., and finally freeze-dried to collect a dry powder of a water extraction product. The final extraction yields of *Cordyceps* polysaccharide and cordycepin in the *Cordyceps militaris* fruiting bodies are 10.13 g/100 g and 5.794 mg/g respectively.

Comparative Example of Example 1: Using a diluted hydrochloric acid solution as extractant, in combination with ultra-low temperature freezing-defrosting to extract *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder; then the dry powder was immersed in a prepared diluted hydrochloric acid solution (pH=4.8), and subjected to three cycles of ultra-low temperature freezing (−80° C.) and microwave defrosting (400 W, for 2 min), and then stirred and extracted for 40 min at 65° C.; then an extract was concentrated to 1% of original volume by rotary evaporation at 60° C. and at 0.095 MPa, and the concentrate was collected and frozen for 24 hours at −70° C., and finally freeze-dried to collect a dry powder of a water extraction product. The final extraction yields of *Cordyceps* polysaccharide and cordycepin in the *Cordyceps militaris* fruiting bodies are 9.09 g/100 g and 4.854 mg/g respectively, which are significantly lower than the yields of the active ingredients in Example 1.

Example 2: Using a citric acid solution as extractant, in combination with ultra-low temperature freezing-defrosting and low-frequency ultrasonic technique to extract *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder, then the dry powder was immersed in a prepared citric acid solution (pH=4.8), and subjected to three cycles of ultra-low temperature freezing (−80° C.) and microwave defrosting (400 W, for 2 min), and at the same time, with assistance of low-frequency ultrasonic waves (having a frequency of 20-30 KHz, and a power of 350 W), stirred and extracted for 40 min at 65° C.; then an extract was concentrated to 1% of original volume by rotary evaporation at 60° C. and at 0.095 MPa; and the concentrate was collected and frozen for 24 hours at −70° C., and finally freeze-dried to collect a dry powder of a water extraction product. The final extraction yields of *Cordyceps* polysaccharide and cordycepin in the *Cordyceps militaris* fruiting bodies are 10.09 g/100 g and 5.721 mg/g respectively.

Comparative Example of Example 2: Using a citric acid solution as extractant, in combination with low-frequency ultrasonic technique to extract *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder, then the dry powder was immersed in a prepared citric acid solution (pH=4.8), and by use of low-frequency ultrasonic waves (having a frequency of 20-30 KHz, and a power of 350 W), stirred and extracted for 40 min at 65° C.; then an extract was concentrated to 1% of original volume by rotary evaporation at 60° C. and at 0.095 MPa; and the concentrate was collected and frozen for 24 hours at −70° C., and finally freeze-dried to collect a dry powder of a water extraction product. The final extraction yields of *Cordyceps* polysaccharide and cordycepin in the *Cordyceps militaris* fruiting bodies are 9.17 g/100 g and 4.911 mg/g respectively, which are obviously lower than the yields of *Cordyceps* polysaccharide and cordycepin in Example 2.

Example 3: Using an acetic acid solution as extractant, in combination with ultra-low temperature freezing-defrosting and low-frequency ultrasonic technique to extract *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder, then the dry powder was immersed in a prepared acetic acid solution (pH=4.9), and subjected to three cycles of ultra-low temperature freezing (−80° C.) and microwave defrosting (400 W, for 2 min), and at the same time, with assistance of low-frequency ultrasonic waves (having a frequency of 20-30 KHz, and a power of 350 W), stirred and extracted for 40 min at 65° C.; then an extract was concentrated to 1% of original volume by rotary evaporation at 60° C. and at 0.095 MPa; and the concentrate was collected and frozen for 24 h at −70° C., and finally freeze-dried to collect a dry powder of a water extraction product. The final extraction yields of *Cordyceps* polysaccharide and cordycepin in the *Cordyceps militaris* fruiting bodies are 10.17 g/100 g and 5.682 mg/g respectively.

Comparative Example of Example 3: Using an acetic acid solution as extractant, in combination with low-frequency ultrasonic technique to extract *Cordyceps* polysaccharide and cordycepin in *Cordyceps militaris* fruiting bodies

*Cordyceps militaris* fruiting bodies were picked, washed, dried, pulverized and degreased to obtain a *Cordyceps militaris* leftover dry powder, then the dry powder was immersed in a prepared acetic acid solution (pH=4.9), and by use of low-frequency ultrasonic waves (having a frequency of 20-30 KHz, and a power of 350 W), stirred and extracted for 40 min at 65° C.; then an extract was concentrated to 1% of original volume by rotary evaporation at 60° C. and at 0.095 MPa; and the concentrate was collected and frozen for 24 hours at −70° C., and finally freeze-dried to collect a dry powder of a water extraction product. The final extraction yields of *Cordyceps* polysaccharide and cordycepin in the *Cordyceps militaris* fruiting bodies are 9.08 g/100 g and 4.782 mg/g respectively, which are obviously lower than the yields of the active ingredients in Example 3.

What is claimed is:

1. An ultrasonic composite acidic water extraction method for a *Cordyceps* polysaccharide and cordycepin in *Cordyceps militaris*, comprising the following specific steps:
   (1) culturing and harvesting: culturing *Cordyceps militaris* fruiting bodies in a solid medium, harvesting after 40-45 days of the culturing, and storing the harvested *Cordyceps militaris* fruiting bodies under refrigeration at 4° C.;
   (2) washing and drying: drying the harvested *Cordyceps militaris* fruiting bodies for 5 hours in a hot-air drying oven at 60-65° C. during which the *Cordyceps militaris* fruiting bodies are arranged evenly and kept ventilated; and collecting and storing same in a cool and dry place after drying to a constant weight;
   (3) pulverizing: crushing a dry sample of *Cordyceps militaris*, and passing through a 60-mesh sieve;
   (4) degreasing: placing the pulverized sample in a reflux device, performing reflux extraction with 95% ethanol at a material-liquid ratio of 1:5 (w:v) in a boiling water bath for 3 hours, centrifugation, collecting the precipitate, and drying at 60-65° C. to a constant weight, to obtain a degreased *cordyceps* powder;
   (5) ultra-low temperature freezing-microwave defrosting cycle: adding distilled water into the degreased *cordyceps* powder at a material-liquid ratio of 1:40 (w:v), to obtain an extract; stirring and titrating the extract with 1 mol/L of a diluted acid solution to obtain a pH of 4.8±0.2; freezing the extract for 2 hours at −80° C.; taking out the extract, and defrosting for 2-3 min using microwaves with a power of 300-400 W; and repeating the freezing and the defrosting operations three times, to obtain a crude extraction mixture of *Cordyceps militaris*;
   (6) ultrasonic-assisted extraction: after obtaining the crude extraction mixture of *Cordyceps militaris*, extracting for 35-40 min at 65-70° C. with the assistance of ultrasonic waves having a frequency of 20-30 KHZ and a power of 300-400 W; and after the ultrasonic-assisted extraction is complete, centrifuging for 15 min at 4,000 r/min, and filtering the supernatant to obtain a crude water extract of the *Cordyceps militaris* fruiting bodies;

(7) evaporation and concentration: concentrating, by rotary evaporation at 60-65° C. and at 0.095 MPa, the crude water extract of the *Cordyceps militaris* fruiting bodies to 1% of the original volume, until it finally becomes a viscous and thick slurry; collecting the concentrated crude water extract of the *Cordyceps militaris* fruiting bodies, and freezing for 24 hours at −70° C.; and (8) freeze-drying to prepare powder: performing freeze-drying on the frozen concentrated crude water extract of the *Cordyceps militaris* fruiting bodies for 3 hours in a cold trap at −55° C., to obtain a dry powder of the crude water extract of the *Cordyceps militaris* fruiting bodies.

2. The ultrasonic composite acidic water extraction method for a *Cordyceps* polysaccharide and cordycepin in *Cordyceps militaris* according to claim 1, wherein in the step (1), components of the solid medium comprise rice, wheat, glucose, potassium dihydrogen phosphate, magnesium sulfate heptahydrate, vitamin B1, and vitamin B2.

3. The ultrasonic composite acidic water extraction method for a *Cordyceps* polysaccharide and cordycepin in *Cordyceps militaris* according to claim 1, wherein in the step (1), a height of the harvested *Cordyceps militaris* fruiting bodies is greater than or equal to 7 cm.

4. The ultrasonic composite acidic water extraction method for a *Cordyceps* polysaccharide and cordycepin in *Cordyceps militaris* according to claim 1, wherein in the step (3), the dry sample of *Cordyceps militaris* is cut into segments of 3-4 cm for crushing, and then is pulverized.

5. The ultrasonic composite acidic water extraction method for a *Cordyceps* polysaccharide and cordycepin in *Cordyceps militaris* according to claim 2, wherein in the step (3), the dry sample of *Cordyceps militaris* is cut into segments of 3-4 cm for crushing, and then is pulverized.

6. The ultrasonic composite acidic water extraction method for a *Cordyceps* polysaccharide and cordycepin in *Cordyceps militaris* according to claim 1, wherein in the step (4), a speed of the centrifugation is 4,000 r/min, and a time of the centrifugation is 20 min.

7. The ultrasonic composite acidic water extraction method for a *Cordyceps* polysaccharide and cordycepin in *Cordyceps militaris* according to claim 2, wherein in the step (4), a speed of the centrifugation is 4,000 r/min, and a time of the centrifugation is 20 min.

8. The ultrasonic composite acidic water extraction method for a *Cordyceps* polysaccharide and cordycepin in *Cordyceps militaris* according to claim 3, wherein in the step (4), a speed of the centrifugation is 4,000 r/min, and a time of the centrifugation is 20 min.

9. The ultrasonic composite acidic water extraction method for a *Cordyceps* polysaccharide and cordycepin in *Cordyceps militaris* according to claim 1, wherein in the step (5), the diluted acid solution is a diluted hydrochloric acid solution, a citric acid solution or an acetic acid solution.

10. The ultrasonic composite acidic water extraction method for a *Cordyceps* polysaccharide and cordycepin in *Cordyceps militaris* according to claim 2, characterized in that, wherein in the step (5), the diluted acid solution is a diluted hydrochloric acid solution, a citric acid solution or an acetic acid solution.

11. The ultrasonic composite acidic water extraction method for a *Cordyceps* polysaccharide and cordycepin in *Cordyceps militaris* according to claim 2, wherein in the step (1), a height of the harvested *Cordyceps militaris* fruiting bodies is greater than or equal to 7 cm.

12. The ultrasonic composite acidic water extraction method for a *Cordyceps* polysaccharide and cordycepin in *Cordyceps militaris* according to claim 3, wherein in the step (3), the dry sample of *Cordyceps militaris* is cut into segments of 3-4 cm for crushing, and then is pulverized.

13. The ultrasonic composite acidic water extraction method for a *Cordyceps* polysaccharide and cordycepin in *Cordyceps militaris* according to claim 3, wherein in the step (5), the diluted acid solution is a diluted hydrochloric acid solution, a citric acid solution or an acetic acid solution.

14. The ultrasonic composite acidic water extraction method for a *Cordyceps* polysaccharide and cordycepin in *Cordyceps militaris* according to claim 4, wherein in the step (4), a speed of the centrifugation is 4,000 r/min, and a time of the centrifugation is 20 min.

15. The ultrasonic composite acidic water extraction method for a *Cordyceps* polysaccharide and cordycepin in *Cordyceps militaris* according to claim 4, wherein in the step (5), the diluted acid solution is a diluted hydrochloric acid solution, a citric acid solution or an acetic acid solution.

16. The ultrasonic composite acidic water extraction method for a *Cordyceps* polysaccharide and cordycepin in *Cordyceps militaris* according to claim 6, wherein in the step (5), the diluted acid solution is a diluted hydrochloric acid solution, a citric acid solution or an acetic acid solution.

\* \* \* \* \*